United States Patent [19]

Ohtaka et al.

[11] Patent Number: 4,703,048

[45] Date of Patent: Oct. 27, 1987

[54] NOVEL 1-BENZHYDRYL-4-CINNAMYLPIPERAZINE DERIVATIVES, AND PHARMACEUTICAL COMPOSITIONS COMPRISING SAID COMPOUNDS AS ACTIVE INGREDIENT FOR TREATING A CEREBROVASCULAR DISEASE

[75] Inventors: Hiroshi Ohtaka; Toshiro Kanazawa; Keizo Ito, all of Osaka; Goro Tsukamoto, Toyonaka, all of Japan

[73] Assignee: Kanebo Ltd., Tokyo, Japan

[21] Appl. No.: 815,452

[22] Filed: Dec. 31, 1985

[30] Foreign Application Priority Data

Jan. 11, 1985 [JP] Japan .................................. 60-3696

[51] Int. Cl.⁴ .................. A61K 31/495; C07D 295/08
[52] U.S. Cl. ...................................... 514/255; 544/396
[58] Field of Search ........................ 544/396; 514/255

[56] References Cited

U.S. PATENT DOCUMENTS

| | | | |
|---|---|---|---|
| 3,773,939 | 11/1973 | Janssen | 514/255 |
| 3,957,790 | 5/1976 | Suzuki et al. | 544/396 |
| 4,008,324 | 2/1977 | Metz et al. | 544/396 |
| 4,528,194 | 7/1985 | Masaki | 544/396 |
| 4,663,325 | 5/1987 | Ohtaka et al. | 544/396 |

FOREIGN PATENT DOCUMENTS

| | | | |
|---|---|---|---|
| 556791 | 5/1957 | Belgium | 544/396 |
| 152799 | 8/1985 | European Pat. Off. | |
| 159566 | 10/1985 | European Pat. Off. | 544/396 |
| 36478 | 4/1975 | Japan | 544/396 |
| 605873 | 10/1978 | Switzerland | 544/396 |

OTHER PUBLICATIONS

Raabe et al, Chem. 93-186413k.
March, Advanced Org. Chem., 2nd edition, pp. 1119-1121.

Primary Examiner—Donald G. Daus
Assistant Examiner—Cecilia Shen
Attorney, Agent, or Firm—Wenderoth, Lind & Ponack

[57] ABSTRACT

A 1-benzhydryl-4-cinnamylpiperazine derivative represented by the following formula (I)

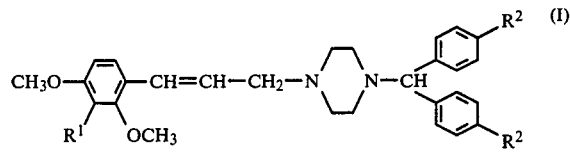

wherein $R^1$ represents a hydrogen atom or a methoxy group, and $R^2$ represents a hydrogen or fluorine atom, or a pharmaceutically acceptable acid addition salt thereof. The compound (I) is prepared by selectively reducing the corresponding 1-benzhydryl-4-cinnamoyl-piperazine derivative and optionally converting the product into its acid addition salt. The compound (I) is useful for treatment of cerebrovascular disease in a human.

11 Claims, No Drawings

NOVEL 1-BENZHYDRYL-4-CINNAMYLPIPERAZINE DERIVATIVES, AND PHARMACEUTICAL COMPOSITIONS COMPRISING SAID COMPOUNDS AS ACTIVE INGREDIENT FOR TREATING A CEREBROVASCULAR DISEASE

This invention relates to novel piperazine derivatives, processes for production thereof, and pharmaceutical compositions comprising the piperazine derivatives as an active ingredient. More specifically, this invention relates to a 1-benzhydryl-4-cinnamylpiperazine derivative represented by the following formula (I)

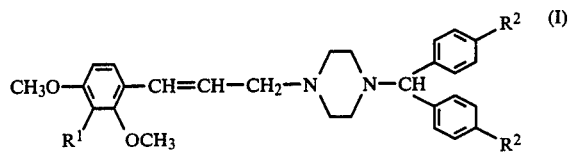

wherein $R^1$ represents a hydrogen atom or a methoxy group, and $R^2$ represents a hydrogen or fluorine atom, or a pharmaceutically acceptable acid addition salt thereof, and an agent for treating cerebrovascular diseases in humans comprising the aforesaid compound as an active ingredient.

The cerebrovascular diseases can roughly be classified as intracranial hemorrhages such as intracerebral hemorrhage or subarachnoid hemorrhage, and cerebral infarctions such as cerebral thrombosis or cerebral embolus, transient ischemic attack, and hypertensive encephalopathy.

In these diseases, a disorder of circulation of the brain parenchyma occurs owing to hemorrhage, thrombus, embolus, etc. within the brain, and leads to an insufficiency in glucose or oxygen which is an energy source for neuronal activity. This results in functional and organic disturbances in the ischemic area. Accordingly, drugs which supply glucose and oxygen to the ischemic area by increasing cerebral blood flow are effective for the treatment and prevention of these diseases.

Previously, various drugs such as cinnarizine have been clinically used for the purpose of treating these cerebrovascular diseases and subsequent complications, preventing relapse, improving their aftereffects, etc.

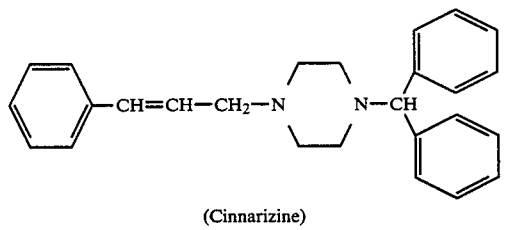

(Cinnarizine)

Belgian Pat. No. 556791 and German Laid-Open Patent Publication No. 1929330 disclose compounds corresponding to cinnarizine having various monosubstituents on the phenyl groups of the benzhydryl group, and their application to allergic diseases and diseases of the circulatory system. In particular, a compound of the following formula, which has a common name "flunarizine", is clinically used in the form of its dihydrocloride as a cerebrovascular drug having superior action and durability compared to cinnarizine.

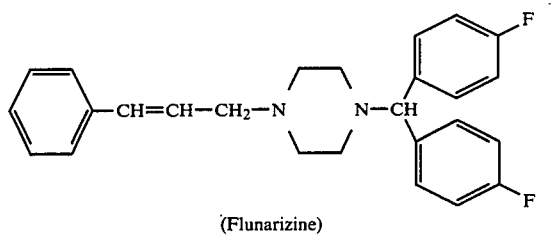

(Flunarizine)

The laid-open specification of EP-152799A laid-open after the priority date of the present application discloses 1-[bis(4-fluorophenyl)methyl]-4-(3,4-dimethoxycinnamyl)piperazine of the following formula and its pharmaceutically acceptable salts.

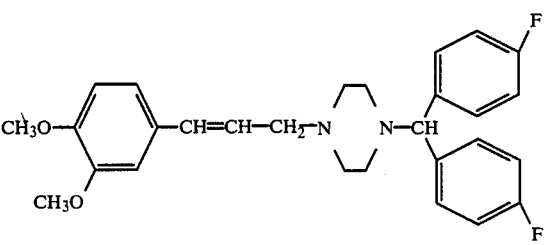

It is an object of this invention to provide a novel 1-benzhydryl-4-cinnamylpiperazine derivative or its pharmaceutically acceptable acid addition salt.

Another object of this invention is to provide a novel 1-benzhydryl-4-cinnamylpiperazine derivative or its pharmaceutically acceptable acid addition salt having an action of treating cerebrovascular diseases.

Still another object of this invention is to provide a process for producing a novel 1-benzhydryl-4-cinnamylpiperazine derivative or its pharmaceutically acceptable acid addition salt.

These objects and advantages of this invention are achieved in accordance with this invention by a 1-benzhydryl-4-cinnamylpiperazine derivative represented by the following formula (I)

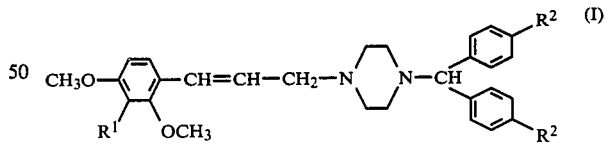

wherein $R^1$ represents a hydrogen atom or a methoxy group, and $R^2$ represents a hydrogen or fluorine atom, or a pharmaceutically acceptable acid addition salt thereof.

Specifically, the compounds of this invention are the following four compounds and their pharmaceutically acceptable acid addition salts. The acid addition salts include, for example, salts with inorganic acids such as hydrochloric acid, hydrobromic acid or sulfuric acid, and organic acids such as maleic acid, fumaric acid, succinic acid and citric acid.

1-[bis(4-fluorophenyl)methyl]-4-(2,3,4-trimethoxycinnamyl)piperazine;

1-benzhydryl-4-(2,3,4-trimethoxycinnamyl)piperazine;

1-[bis(4-fluorophenyl)methyl]-4-(2,4-dimethoxycin-namyl)piperazine; and
1-benzhydryl-4-(2,4-dimethoxycinnamyl)piperazine.

By animal experiments, the compounds of this invention have been found to show an excellent action of increasing cerebral blood flow.

For example, in an experiment using dogs, the compounds of this invention have a stronger and longer lasting action of increasing cerebral blood flow than cinnarizine, a popular cerebrovascular disease treatment agent, or flunarizine dihydrochloride, an improved drug of cinnarizine, in intravenous administration (see Test Example 1 given hereinbelow).

These facts indicate that the compounds of this invention are useful as agents for treating cerebrovascular diseases (including therapeutic and prophylactic drugs). As indicated hereinabove, one object of this invention is to provide such drugs.

The compounds of this invention can be produced, for example, by selectively reducing the compound represented by the following formula (II) via the following process and optionally converting the product (I) into its acid addition salt.

mixture and purifying it, and converting the purified acid addition salt to a free base.

The following pharmacological tests show the utility of the compounds of this invention.

TEST EXAMPLE 1

Activity of increasing cerebral blood flow:
(A) Test compounds
1-[Bis(4-fluorophenyl)methyl]-4-(2,3,4-trimethoxycin-namyl)piperazine dihydrochloride (compound A of the invention).
1-Benzhydryl-4-(2,3,4-trimethoxycinnamyl) piperazine dihydrochloride (compound B of the invention).
1-[Bis(4-fluorophenyl)methyl]-4-(2,4-dimethoxycin-namyl)piperazine fumarate (compound C of the invention).
1-Benzhydryl-4-(2,4-dimethoxycinnamyl) piperazine fumarate (compound D of the invention).
Cinnarizine (control compound).
Flunarizine dihydrochloride (control compound).
(B) Testing method The activity of increasing cerebral blood flow was measured by using the amount of vertebral blood flow

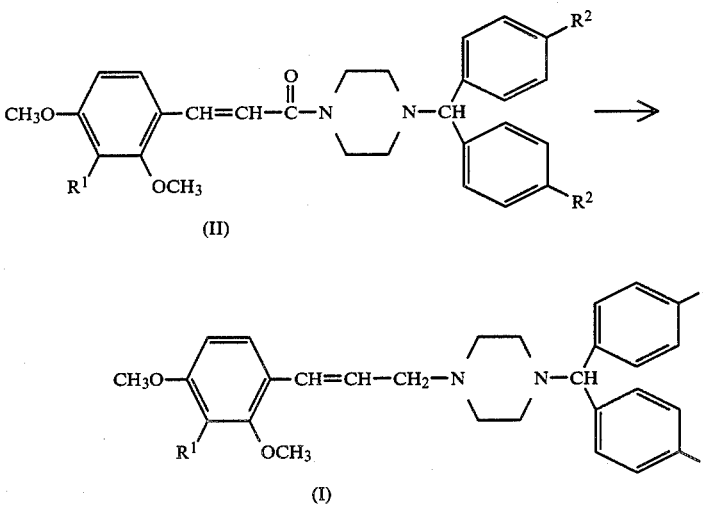

(In the formulae, $R^1$ and $R^2$ are the same as defined hereinabove.)

Specifically, the compound of formula (I) can be produced by suspending or dissolving the compound of formula (II) in a customary manner in a solvent such as diethyl ether, and treating the suspension or solution with an equimolar proportion, or a slight excess, of a reducing agent such as lithium aluminum hydride or sodium bis(2-methoxyethoxy)aluminum hydride under ice cooling or at temperatures up to room temperature.

The compound of this invention produced by the above process is isolated from the reaction product preferably in the form of an acid addition salt and purified. As required, it may be converted in a customary manner to a free base or other various acid addition salts.

The compound (II) can be produced, for example, by reacting 2,4-dimethoxy- or 2,3,4-trimethoxycinnamic acid with benzhydrylpiperazine or bis(4-fluorophenyl) methylpiperazine or its salt either directly or after converting the cinnamic acid to its halide, thereafter isolating the product in the form of an acid addition salt such as a hydrochloride or a fumarate from the reaction as an index. Mongrel dogs of either sex (body weight 11 to 14 kg; four per group) were anesthetized with sodium pentobarbital (30 mg/kg, by intravenous injection), and the right vertebral artery was isolated from the surrounding tissues. A flow probe was attached to it and led to an electromagnetic flow meter (MFV-2100 made by Nihon Kohden Co., Ltd.). The amount of blood flow was periodically measured [see Meth and Find Exptl Clin Pharmacol, 3 (6), 397 (1981)]. Each of the test compounds was dissolved in a 2% tartaric acid solution containing 20% dimethylacetamide, and injected into the right femoral vein.

Each of the test compunds was administered in a dose range of 0.03 to 0.3 mg/kg, and doses which increased the cerebral blood flow by 50% (VBF-ED$_{50}$) were calculated from the regression line.

Furthermore, each of the test compounds was administered in a dose of 0.3 mg/kg, and increases (%) in vertebral blood flow were determined 1, 5, 10 and 20 minutes after the administration.
(C) Test results The results are shown in Table 1.

TEST EXAMPLE 2

Acute toxicity:

(A) Test compounds

The same compounds as used in Test Example 1 were tested.

(B) Testing method ddY-strain male mice (body weight 18 to 22 g; five per group) were caused to fast 24 hours. Then, each of the test compounds was administered orally, and acute toxicity values ($LD_{50}$) were determined.

Each of the compounds was dissolved or suspended in a 2% tartaric acid solution containing 20% of dimethylacetamide, and orally administered to the animals. From the number of animals which died during seven days, the $LD_{50}$ values were calculated by using the Weil method.

(C) Test results

The results are shown in Table .

TABLE 1

| | | Activity of increasing cerebral blood flow | | | | |
|---|---|---|---|---|---|---|
| | | Increase (%) in vertebral blood flow (mean ± standard error) Time elapsed after administration (minutes) | | | | | Acute toxicity |
| Test Compound | | 1 | 5 | 10 | 20 | $VBF\text{-}ED_{50}$ (mg/kg) | $LD_{50}$ (mg/kg) |
| Compounds | A | 107 ± 17 | 137 ± 39 | 134 ± 40 | 120 ± 38 | 0.06 | 185 |
| of the | B | 76 ± 14 | 58 ± 12 | 41 ± 7 | 26 ± 4 | 0.12 | 841 |
| Invention | C | 83 ± 12 | 92 ± 10 | 71 ± 7 | 50 ± 7 | 0.08 | 102 |
| | D | 66 ± 11 | 51 ± 10 | 27 ± 7 | 18 ± 6 | 0.18 | 773 |
| Cinnarizine | | 40 ± 10 | 5 ± 4 | 2 ± 2 | 2 ± 4 | >0.3 | >2000 |
| Flunarizine dihydrochloride | | 53 ± 20 | 20 ± 12 | 11 ± 7 | 10 ± 6 | >0.3 | 285 |

TEST EXAMPLE 3

The activity of compound A of the invention to increase cerebral blood flow was examined by intraduodenal administration.

(A) Testing method

Compound A was dissolved in a 2% tartaric acid solution containing 20% dimethylacetamide, and administered intraduodenally to mongrel dogs of either sex (body weight 11–18 kg, five per group) in a dose of 1 mg/kg.

At 10, 30, 60, 120, 180 and 240 minutes after the administration, the increase (%) of vertebral blood flow was measured in the same way as in Test Example 1.

(B) Test Results

The results are shown in Table 2.

TABLE 2

| Time after administration (minutes) | Increase (%) of vertebral blood flow (mean ± standard error) |
|---|---|
| 10 | 6.2 ± 1.8 |
| 30 | 51.0 ± 18.6 |
| 60 | 149.3 ± 48.0 |
| 120 | 150.9 ± 38.2 |
| 180 | 98.8 ± 24.2 |
| 240 | 55.1 ± 17.2 |

The foregoing results (Table 1) of the pharmacological tests demonstrate that the compounds of this invention have stronger and longer lasting activities of increasing cerebral blood flow than cinnarizine or flunarizine dihydrochloride.

The compounds of this invention are administered to humans having cerebrovascular diseases in amouns effective for treating the cerebrovascular diseases.

The compounds of this invention are administered to humans, for example, orally, or intravenously, preferably orally. For oral administration, the compounds of this invention, particularly their acid addition salts, are formed into tablets, granules, powders or capsules containing suitable amounts of granules or powders by a conventional method together with usual drug additives. Examples of the drug additives are vehicles such as lactose, synthetic aluminum silicate, glucose and mannitol, disintegrants such as carboxymethyl cellulose and sodium arginate, lubricants such as magnesium stearate and talc and binders such as corn starch and polyvinyl pyrrolidone.

The dose of the compounds of this invention varies depending upon the condition, body weight, age, etc. of the patient. Usually, the compound of the invention is administered either once or two or three times daily in a dose of about 0.01 to 1.0 mg/kg (calculated as free base) per adult per day.

The following Referential Examples and Examples illustrate the present invention more specifically.

REFERENTIAL EXAMPLE 1

Production of 1-[bis(4-fluorophenyl)methyl]-4-(2,3,4-trimethoxycinnamoyl)piperazine hydrochloride:

In 10 ml of chloroform was suspended 2.5 g (10.5 millimoles) of 2,3,4-trimethoxycinnamic acid, and under ice cooling, 3.5 ml (about 48 millimoles) of thionyl chloride was added dropwise. The mixture was stirred for 30 minutes under ice cooling, and the excess of thionyl chloride and chloroform were distilled off under reduced pressure. The residue was diluted with 20 ml of methylene chloride and added dropwise under ice cooling to 30 ml of a methylene chloride solution of 2.7 g (9.4 millimoles) of bis(4-fluorophenyl)methylpiperazine and 2 g (19.8 millimoles) of triethylamine. The mixture was stirred for 30 minutes under ice cooling. Thereafter, a 10% aqueous solution of sodium bicarbonate was added, and the mixture was shaken. The organic layer was separated, washed with water, and dried over anhydrous magnesium sulfate. The solvent was distilled off under reduced pressure. The resulting oily product was diluted with 20 ml of ethanol. One milliliter of concentrated hydrochloric acid was added and then ether was added. The crystals that precipitated were collected by filtration. Recrystallization from methanol gave 1.4 g (yield 27.3%) of 1-[bis(4-fluorophenyl)methyl]-4-(2,3,4-trimethoxycinnamoyl)piperazine hydrochloride as colorless crystals.

Melting point: 225°–229° C. (decomp.)

NMR(CD$_3$OD-D$_2$O, δppm): 3.1-3.5(4H), 3.82(3H, s), 3.88(6H, s), 4.0-4.4(4H), 5.56(1H, s), 6.7-8.1(12H, m).

Elemental analysis for C$_{29}$H$_{30}$F$_2$N$_2$O$_4$·HCl: Calculated (%): C,63.91; H,5.73; N,5.14. Found (%): C,63.69; H,5.60; N,5.31.

REFERENTIAL EXAMPLE 2

Production of 1-benzhydryl-4-(2,3,4-trimethoxycinnamoyl)piperazine hydrochloride:

In 10 ml of chloroform was suspended 2.5 g (10.5 millimoles) of 2,3,4-trimethoxycinnamic acid, and under ice cooling, 3.5 ml (about 48 millimoles) of thionyl chloride was added dropwise. The mixture was stirred for 30 minutes under ice cooling, and the excess of thionyl chloride and chloroform were distilled off under reduced pressure. The residue was diluted with 20 ml of methylene chloride, and added dropwise under ice cooling to 30 ml of a methylene chloride solution of 2.5 g (9.9 millimoles) of benzhydrylpiperazine and 2 g (19.8 millimoles) of triethylamine. The mixture was stirred for 30 minutes under ice cooling. A 10% aqueous solution of sodium bicarbonate was added, and the mixture was shaken. The organic layer was separated, washed with water, and dried over anhydrous magnesium sulfate. The solvent was distilled off under reduced pressure. The resulting oily product was diluted with 20 ml of ethanol. One milliliter of concentrated hydrochloric acid was added, and then ether was added. The crystals that precipitated were collected by filtration. Recrystallization from ethanol gave 2.2 g (yield 43.7%)of 1-benzhydryl-4-(2,3,4-trimethoxycinnamoyl)piperazine hydrochloride as colorless crystals.

Melting point: 207°-209° C. (decomp.)

NMR(CD$_3$OD-D$_2$O, δppm): 3.1-3.6(4H), 3.82(3H, s), 3.87(6H, s), 4.0-4.4(4H), 5.5(1H, s), 6.6-8.2(14H, m).

Elemental analysis for C$_{29}$H$_{32}$N$_2$O$_4$·HCl: Calculated (%): C,68.43; H,6.53; N,5.50 Found (%): C,68.32; H,6.60; N,5.56

REFERENTIAL EXAMPLE 3

Production of 1-[bis(4-fluorophenyl)methyl]-4-(2,4-dimethoxycinnamoyl)piperazine hemifumarate:

In 100 ml of chloroform was suspended 25 g (120 millimoles) of 2,4-dimethoxycinnamic acid, and at room temperature, 44 ml (about 600 millimoles) of thionyl chloride was added dropwise. The mixture was stirred at room temperature for 2 hours, and the excess of thionyl chloride and chloroform were distilled off under reduced pressure. The residue was diluted with 200 ml of chloroform, and added dropwise at room temperature to 300 ml of a chloroform solution of 34.6 g (120 millimoles) of bis(4-fluorophenyl)methylpiperazine and 24.3 g (240 millimoles) of triethylamine. The mixture was stirred at room temperature for 2 hours, and then a 10% aqueous solution of sodium bicarbonate was added. The mixture was shaken, and the organic layer was separated, washed with water, and dried over anhydrous magnesium sulfate. The solvent was distilled off under reduced pressure. To the resulting oily product was added 200 ml of an ethanol solution of 14 g of fumaric acid. The crystals that precipitated were collected by filtratiion. Recrystallization from chloroform/methanol (1/1, v/v) gave 18.8 g (yield 29.2%) of 1-[bis(4-fluorophenyl)methyl]-4-(2,4-dimethoxycinnamoyl)piperazine hemifumarate as colorless crystals.

Melting point: 195°-197° C.

NMR(DMSO-d$_6$, δppm): 2.0-2.7(4H), 3.3-4.0(4H), 3.82(3H, s), 3.87(3H, s), 4.4(1H, s), 6.3-8.0(14H, m).

Elemental analysis for C$_{28}$H$_{28}$F$_2$N$_2$O$_3$·½C$_4$H$_4$O$_4$: Calculated (%): C,67.15; H,5.64; N,5.22. Found (%): C,67.11; H,5.68; N,5.27.

REFERENTIAL EXAMPLE 4

Production of 1-benzhydryl-4-(2,4-dimethoxycinnamoyl)piperazine hydrochloride:

In 100 ml of chloroform was suspended 25 g (120 millimoles) of 2,4-dimethoxycinnamic acid. At room temperature, 44 ml (about 600 millimoles) of thionyl chloride was added dropwise. The mixture was stirred at room temperature for 1.5 hours, and the excess of thionyl chloride and chloroform were distilled off. The residue was diluted with 200 ml of chloroform, and added dropwise at room temperature to 300 ml of of a chloroform solution of 30.2 g (120 millimoles) of benzhydrylpiperazine and 24.3 g (240 millimoles) of triethylamine. The mixture was stirred at room temperature for 3 hours, and then a 10% aqueous solution of sodium bicarbonate was added. The mixture was shaken and the organic layer was separated, washed with water, and dried over anhydrous magnesium sulfate. The solvent was distilled off under reduced pressure. The resulting oily product was diluted with 200 ml of ethanol, and 15 ml of concentrated hydrochloric acid was added. The crystals precipitated were collected by filtration. Recrystallization from hydrous methanol gave 22.7 g (yield 39.5%) of 1-benzhydryl-4-(2,4-dimethoxycinnamoyl)piperazine hydrochloride as pale yellow crystals.

Melting point: 239°-241° C. (decomp.).

NMR(CD$_3$OD-D$_2$O, δppm): 3.2-3.5(4H), 3.88(3H, s), 3.92(3H, s), 3.9-4.2(4H), 5.44(1H, s), 6.5-8.1(15H, m).

Elemental analysis for C$_{28}$H$_{30}$N$_2$O$_3$·HCl: Calculated (%): C,70.21; H,6.52; N,5.85. Found (%): C,70.07; H,6.53; N,5.87.

EXAMPLE 1

Production of 1-[bis(4-fluorophenyl)methyl]-4-(2,3,4-trimethoxycinnamyl)piperazine dihydrochloride:

26.8 g (49.2 millimoles) of 1-[bis(4-fluorophenyl)methyl]-4-(2,3,4-trimethoxycinnamoyl)piperazine hydrochloride obtained in accordance with Referential Example 1 was suspended in a two-layer solution of ethyl acetate and water (1/1, v/v), and with stirring, a 20% aqueous solution of sodium hydroxide was added to adjust the pH of the aqueous layer to 9. The ethyl acetate layer was separated, washed with water, and dried over anhydrous magnesium sulfate. The solvent was distilled off under reduced pressure. The resulting free base was added to 450 ml of anhydrous diethyl ether, and 1.87 g (49.3 millimoles) of lithium aluminum hydride was added little by little at room temperature. The mixture was then stirred for 4 hous at room temperature. Water was added little by little, and then 3N hydrochloric acid was added to make the mixture nearly neutral. The organic layer was separated, washed with water, and dried over anhydrous magnesium sulfate. The solvent was distilled off under reduced pressure. The resulting oily product was diluted with 200 ml of ethanol. Ten milliliters of concentrated hydrochloric acid was added, and then diethyl ether was added. The crystals that precipitated were collected by filtration. Recrystallization from ethanol gave 6.8 g (yield 24.3%) of 1-[bis(4-fluorophenyl)methyl]-4-(2,3,4-trimethoxycinnamyl)piperazine dihydrochloride as colorless crystals.

Melting point: 205°-212° C. (decomp.).

NMR(DMSO-d$_6$, δppm): 3.0–4.3(10H, m), 3.73(3H, s), 3.77(3H, s), 3.80(3H, s), 5.4–8.2(13H, m).

Elemental analysis for C$_{29}$H$_{32}$F$_2$N$_2$O$_3$.2HCl: Calculated (%): C,61.38; H,6.04; N,4.94. Found (%): C,61.52; H,5.89; N,5.08.

By substantially the same procedure as above, 1-[bis(4-fluorophenyl)methyl]-4-(2,3,4-trimethoxycinnamyl)piperazine fumarate was produced. The physical property values and elemental analysis values of this compound were as follows:

Appearance: Colorless crystals
Melting point: 230°–231° C. (decomp.).
NMR(DMSO-d$_6$, δppm): 2.20–3.0(8H, m), 3.0–3.5(2H, broad d), 3.76(6H, s), 3.80(3H, s), 4.46(1H, broad s), 5.7–7.6(12H, m), 6.62(2H, s).

Elemental analysis for C$_{29}$H$_{32}$F$_2$N$_2$O$_3$.C$_4$H$_4$O$_4$: Calculated (%): C,64.91; H,5.94; N,4.59. Found (%): C,64.46; H,6.09; N,4.66.

EXAMPLE 2

Production of 1-benzhydryl-4-(2,3,4-trimethoxycinnamyl)piperazine dihydrochloride:

27.0 g (53millimoles) of 1-benzhydryl-4-(2,3,4-trimethoxycinnamoyl)piperazine hydrochloride obtained in accordance with Referential Example 2 was converted to a free base by the same procedure as in Example 1. The free base was added to 440 ml of anhydrous diethyl ether, and 2.01 g (53 millimoles) of lithium aluminum hydride was added little by little at room temperature. The mixture was then stirred for 6 hours at room temperature. Water was added little by little, and then 3N hydrochloric acid was added to make the mixture nearly neutral. The organic layer was separated, washed with water, and dried over anhydrous magnesium sulfate. The solvent was distilled off under reduced pressure. The resulting oily product was diluted with 200 ml of ethanol, and 10 ml of concentrated hydrochloric acid was added. The crystals that precipitated were collected by filtration. Recrystallization from ethanol gave 5.6 g (yield 20%) of 1-benzhydryl-4-(2,3,4-trimethoxycinnamyl)piperazine dihydrochloride as colorless crystals.

Melting point: 230°–234° C. (decomp.).
NMR(DMSO-d$_6$, δppm): 3.0–4.2(10H, m), 3.75(3H, s), 3.78(3H, s), 3.80(3H, s), 5.2–8.3(15H, m).

Elemental analysis for C$_{29}$H$_{34}$N$_2$O$_3$.2HCl: Calculated (%): C,65.53; H,6.83; N,4.27. Found (%): C, 65.35; H,6.79; N,5.42.

By substantially the same procedure as above, 1-benzhydryl-4-(2,3,4-trimethoxycinnamyl)piperazine fumarate was produced. The physical property values and elemental analysis values of this compound were as follows:

Appearance: Colorless crystals
Melting point: 215°–219° C. (decomp.)
NMR(DMSO-d$_6$, δppm): 2.0–2.9(8H, m), 3.1–3.4(2H, broad d), 3.75(6H, s), 3.80(3H, s), 4.3(1H, s), 5.7–8.0(14H, m), 6,60(2H, s).

Elemental analysis for C$_{29}$H$_{34}$N$_2$O$_3$.C$_4$H$_4$O$_4$: Calculated (%): C,68.97; H,6.67; N,4.87. Found (%): C,68.72; H,6.62; N,4.96.

EXAMPLE 3

Production of 1-[bis(4-fluorophenyl)methyl]-4-(2,4-dimethoxycinnamy)piperazine fumarate:

26.8 g (50 millimoles) of 1-[bis(4-fluorophenyl)methyl]-4-(2,4-dimethoxycinnamoyl)piperazine hemifumarate obtained in accordance with Referential Example 3 was converted to a free base by the same procedure as in Example 1. The free base was added to 440 ml of anhydrous diethyl ether, and 1.9 g (50 millimoles) of lithium aluminum hydride was added little by little at room temperature. Then, the mixture was stirred for 3 hours at room temperature. Water was added little by little, and then 3N hydrochloric acid was added to make the mixture nearly neutral. The organic layer was separated, washed with water, and dried over anhydrous magnesium sulfate. The solvent was distilled off under reduced pressure. A solution of 6 g of fumaric acid in 100 ml of ethanol was added to the resulting oily product. The crystals that precipitated were collected. Recrystallization from ethanol/water (1/1, v/v) gave 9.7 g (yield 32.6%) of 1-[bis(4-fluorophenyl)methyl]-4-(2,4-dimethoxycinnamyl)piperazine fumarate as colorless crystals.

Melting point: 194°–195° C. (decomp.).
NMR(DMSO-d$_6$, δppm): 2.0–2.8(8H, m), 3.0–3.4(2H, broad d), 3.76(6H, s), 4.33(1H, s), 5.7–7.6(13H, m), 6.60(2H, s).

Elemental analysis for C$_{28}$H$_{30}$F$_2$N$_2$O$_2$.C$_4$H$_4$O$_4$: Calculated (%): C,66.20; H,5.90; N,4.82. Found (%): C,66.12; H,5.91; N,4.73.

EXAMPLE 4

Production of 1-benzhydryl-4-(2,4-dimethoxycinnamyl)piperazine fumarate:

28.3 g (59 millimoles) of 1-benzhydryl-4-(2,4-dimethoxycinnamoyl)piperazine hydrochloride obtained in accordance with Referential Example 4 was converted to a free base by the same procedure as in Example 1. The free base was added to 440 ml of anhydrous diethyl ether, and 2.24 g (59 millimoles) of lithium aluminum hydride was added little by little at room temperature. Then, the mixture was stirred for 4 hours at room temperature. Water was added little by little, and then 3N hydrochloric acid was added to make the mixture nearly neutral. The ether layer was separated. Chloroform (200 ml) was added to the aqueous layer, and the mixture was well shaken. The chloroform layer was separated. The ether layer and the chloroform layer was separately washed with water, dried over anhydrous magnesium sulfate, and mixed. The solvents were distilled off under reduced pressure. A solution of 7 g of fumaric acid in 120 ml of ethanol was added to the resulting oily product. The crystals that precipitated were collected by filtration. Recrystallization from ethanol/water (1/1, v/v) gave 7.0 g (yield 26%) of 1-benzhydryl-4-(2,4-dimethoxycinnamyl)piperazine fumarate as colorless crystals.

Melting point: 192°–195° C. (decomp.).
NMR(DMSO-d$_6$, δppm): 2.0–2.9(8H, m), 3.1–3.5(2H, broad d), 3.8(6H, s), 4.3(1H, s), 5.7–7.6(15H, m), 6.65(2H, s).

Elemental analysis for C$_{28}$H$_{32}$N$_2$O$_2$. C$_4$H$_4$O$_4$: Calculated (%): C,70.57; H,6.66; N,5.14. Found (%): C,70.75; H,6.63; N,5.21.

EXAMPLE 5

Production of 1-[bis(4-fluorophenyl)methyl]-4-(2,3,4-trimethoxycinnamyl)piperazine dihydrochloride:

2.72 g (5 millimoles) of 1-[bis(4-fluorophenyl)methyl]-4-(2,3,4-trimethoxycinnamoyl)piperazine hydrochloride obtained in accordance with Referential Example 1 was converted to a free base by the same procedure as in Example 1. The free base was added to 25 ml of toluene, and 2.166 g (7.66 millimoles) of sodium bis(2-methoxyethoxy)aluminum hydride (70 w/w% solution in toluene, Vitride ® made by Hexcel Corporation) was added little by little at room temperature. The mixture was then stirred for 5 minutes at room temperature. Then, 0.8 ml of concentrated hydrochloric acid was added, and the mixture was filtered. To the filtrate was added 1 ml of concentrated hydrochloric acid, and thereafter, the mixture was stirred for 30 minutes. Then, 20 ml of isopropyl ether was added to the mixture. The crystals that precipitated were collected by filtration. Recrystallization from ethanol gave 1.32 g (yield 46.5%) of 1-[bis(4-fluorophenyl)methyl]-4-(2,3,4-trimethoxycinnamyl)piperazine dihydrochloride as colorless crystals.

This compound had the same physical property values and elemental analysis values as those of the product obtained in Example 1.

EXAMPLE 6

Formulation of tablets:
(1) Recipe

| Ingredients | Parts by weight |
|---|---|
| Compound A of the invention | 5 |
| Lactose | 30 |
| Corn starch | 30 |
| Crystalline cellulose | 33 |
| Magnesium stearate | 2 |

(2) Operation
Compound A, i.e. 1-[bis(4-fluorophenyl)methyl]-4-(2,3,4-trimethoxycinnamyl)piperazine dihydrochloride, lactose and crystalline cellulose in the above amounts were uniformly mixed. To the mixed powder was added a 5% aqueous solution of corn starch in an amount of about ¼ of the mixed powder, and the mixture was granulated by the wet granulating method. The remaining corn starch and magnesium stearate were added to the granules, and the mixture was tableted into tablets each weighing 100 mg. Each tablet contained 5 mg of compound A of the invention.

EXAMPLE 7

Formulation of capsules:
(1) Recipe

| Ingredients | Parts by weight |
|---|---|
| Compound A of the invention | 1 |
| Lactose | 74 |
| Crystalline cellulose | 73 |
| Magnesium stearate | 2 |

(2) Operation
The above ingredients were fully mixed to form a uniform mixed powder. The powder was filled in an amount of 150 mg in each of capsules to prepare capsules each containing 1 mg of compound A of the invention.

EXAMPLE 8

Formulation of granules:
(1) Recipe

| Ingredients | Parts by weight |
|---|---|
| Compound A of the invention | 1 |
| Lactose | 50 |
| Corn starch | 49 |

(2) Operation
Compound A and lactose in the above amounts were taken, and corn starch was added as a 5% aqueous solution. The mixture was granulated by the wet granulating method to prepare granules containing 1 mg of compound A per 100 mg.

EXAMPLES 9–11

Tablets (Example 9), capsules (Example 10) and granules (Example 11) each containing the compound B of the invention, i.e. 1-benzhydryl-4-(2,3,4-trimethoxycinnamyl)piperazine dihydrochloride, as an active ingredient were prepared in the same way as in Examples 6, 7 and 8 respectively except that compound B of the invention was used instead of compound A.

EXAMPLES 12–14

Tablets (Example 12), capsules (Example 13) and granules (Example 14) each containing the compound C of the invention, i.e. 1-[bis(4-fluorophenyl)methyl]-4-(2,4-dimethoxycinnamyl)piperazine fumarate, as an active ingredient were prepared in the same way as in Examples 6, 7 and 8 respectively except that compound C of the invention was used instead of compound A.

EXAMPLES 15–17

Tablets (Example 15), capsules (Example 16) and granules (Example 17) each containing the compound D of the invention, i.e. 1-benzhydryl-4-(2,4-dimethoxycinnamyl)piperazine fumarate, as an active ingredient were prepared in the same way as in Examples 6, 7 and 8 respectively except that compound D of the invention was used instead of compound A.

What is claimed is:
1. A 1-benzhydryl-4-cinnamylpiperazine compound of the following formula (I)

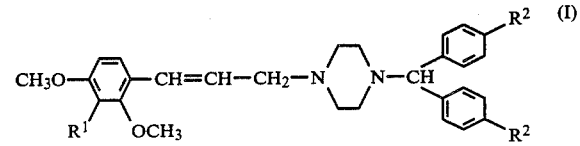

wherein $R^1$ represents a hydrogen atom or a methoxy group, and $R^2$ represents a hydrogen or fluorine atom, or a pharmaceutically acceptable acid addition salt thereof.

2. The compound of claim 1 which is 1-[bis(4-fluorophenyl)methyl]-4-(2,3,4-trimethoxycinnamyl)piperazine or a pharmaceutically acceptable acid addition salt thereof.

3. The compound of claim 1 which is 1-benzhydryl-4-(2,3,4-trimethoxycinnamyl)piperazine or a pharmaceutically acceptable acid addition salt thereof.

4. The compound of claim 1 which is 1-[bis(4-fluorophenyl)methyl]-4-(2,4-dimethoxycinnamyl)piperazine or a pharmaceutically acceptable acid addition salt thereof, 5. The compound of claim 1 which is 1-benzhydryl-4-(2,4-dimethoxycinnamyl)piperazine or a pharmaceutically acceptable acid addition salt thereof.

6. A composition for treating a cerebrovascular disease, comprising a therapeutically effective amount of a 1-benzhydryl-4-cinnamylpiperazine compound of the following formula (I)

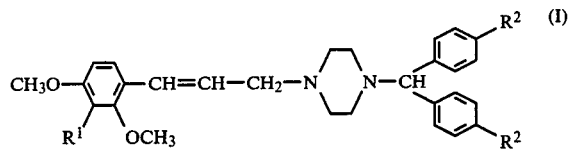

wherein $R^1$ represents a hydrogen atom or a methoxy group, and $R^2$ represents a hydrogen or fluorine atom, or a pharmaceutically acceptable acid addition salt thereof as an active ingredient, and a pharmaceutically acceptable carrier therefor.

7. The composition of claim 6 wherein the active ingredient is 1-[bis(4-fluorophenyl)methyl]-4-(2,3,4-trimethoxycinnamyl)piperazine of a pharmaceutically acceptable acid addition salt thereof.

8. The composition of claim 6 wherein the active ingredient 1-benzhydryl-4-(2,3,4-trimethoxycinnamyl)-piperazine or a pharmaceutically acceptable acid addition salt thereof.

9. The composition of claim 6 wherein the active ingredient is 1-[bis(4-fluorophenyl)methyl]-4-(2,4-dimethoxycinnamyl)piperazine or a pharmaceutically acceptable acid addition salt thereof.

10. The composition of claim 6 wherein the active ingredient is 1-benzhydryl-4-(2,4-dimethoxycinnamyl)-piperazine or a pharmaceutically acceptable acid addition salt thereof.

11. A method for treating a cerebrovascular disease in a human, which comprises administering an amount, effective for treating said cerebrovascular disease, of a 1-benzhydryl-4-cinnamylpiperazine compound of the following formula (I)

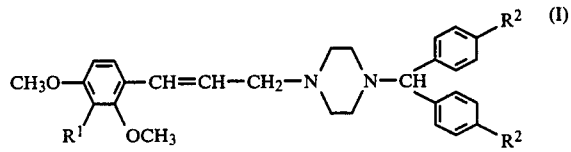

wherein $R^1$ represents a hydrogen atom or a methoxy group, and $R^2$ represents a hydrogen or fluorine atom, or a pharmaceutically acceptable acid addition salt thereof, to a human suffering from the cerebrovascular disease.

* * * * *